(12) United States Patent
Lemke et al.

(10) Patent No.: US 6,804,866 B2
(45) Date of Patent: Oct. 19, 2004

(54) CANNULA CLIP AND ASSOCIATED METHOD OF USE

(76) Inventors: Daniel L. Lemke, Rte. 8, Box 511, Lake City, FL (US) 32055; Imogene G. Lemke, Rte. 8, Box 511, Lake City, FL (US) 32055

( * ) Notice: Subject to any disclaimer, the term of this patent is extended or adjusted under 35 U.S.C. 154(b) by 0 days.

(21) Appl. No.: 10/232,877

(22) Filed: Aug. 30, 2002

(65) Prior Publication Data

US 2003/0188403 A1 Oct. 9, 2003

Related U.S. Application Data

(60) Provisional application No. 60/370,795, filed on Apr. 8, 2002.

(51) Int. Cl.[7] ............................. A44B 21/00; A61M 5/32
(52) U.S. Cl. ............................. 24/338; 24/332; 24/3.11; 604/174
(58) Field of Search ........................ 24/338, 3.11, 3.12, 24/331, 332, 339, 329, 532, 533; 248/317; 604/174, 179

(56) References Cited

U.S. PATENT DOCUMENTS

| | | | |
|---|---|---|---|
| 292,412 A | * | 1/1884 | Covell .......................... 24/332 |
| 915,104 A | | 11/1909 | Montgomery |
| 1,032,436 A | * | 7/1912 | Smith ........................... 24/331 |
| 1,574,695 A | * | 2/1926 | Riley ............................ 24/332 |
| 2,259,817 A | | 2/1941 | Hawkins |
| 2,506,783 A | * | 5/1950 | Fauteux, Jr. .................. 24/532 |
| 3,802,431 A | | 4/1974 | Farr |
| 4,277,864 A | | 7/1981 | Orson, Sr. |
| 4,308,642 A | * | 1/1982 | Heyman ....................... 24/334 |
| 4,333,468 A | | 6/1982 | Geist |
| 4,336,806 A | | 6/1982 | Eldridge, Jr. |
| 4,406,283 A | | 9/1983 | Bir |
| 4,422,456 A | | 12/1983 | Tiep |
| 4,480,639 A | | 11/1984 | Peterson et al. |
| 4,559,941 A | | 12/1985 | Timmons et al. |
| 4,639,980 A | | 2/1987 | Peterson |
| 4,665,566 A | | 5/1987 | Garrow |
| 4,699,139 A | | 10/1987 | Marshall et al. |
| 4,707,906 A | | 11/1987 | Posey |
| 4,739,757 A | | 4/1988 | Edwards |
| 4,742,824 A | | 5/1988 | Payton et al. |
| 4,808,160 A | | 2/1989 | Timmons et al. |
| 4,820,274 A | * | 4/1989 | Choksi et al. .............. 604/174 |
| 4,823,789 A | | 4/1989 | Beisang, III |
| 4,835,824 A | * | 6/1989 | Durham et al. ................ 24/339 |
| 4,836,200 A | | 6/1989 | Clark |
| 4,915,104 A | | 4/1990 | Marcy |
| 4,949,733 A | | 8/1990 | Sampson |
| 4,995,384 A | | 2/1991 | Keeling |
| 5,025,805 A | | 6/1991 | Nutter |
| 5,193,534 A | | 3/1993 | Peppler |
| 5,308,337 A | | 5/1994 | Bingisser |
| 5,438,979 A | | 8/1995 | Johnson, Jr. et al. |
| 5,507,460 A | * | 4/1996 | Schneider .................... 248/339 |
| 5,558,090 A | | 9/1996 | James |
| 5,645,058 A | | 7/1997 | Odom |
| 5,666,702 A | * | 9/1997 | Ming-Chieh .................. 24/338 |
| 5,704,916 A | | 1/1998 | Byrd |
| 5,709,665 A | * | 1/1998 | Vergano et al. .............. 604/174 |
| 5,774,950 A | * | 7/1998 | Stout ............................ 24/3.13 |
| 6,026,811 A | | 2/2000 | Settle |
| 6,523,231 B1 | * | 2/2003 | Lassiter ........................ 24/339 |

* cited by examiner

Primary Examiner—Robert J. Sandy
(74) Attorney, Agent, or Firm—Saliwanchik, Lloyd & Saliwanchik

(57) ABSTRACT

A clip for holding cannula so as to alleviate ear discomfort by reducing the weight and tension created by the cannula. The present invention includes a clip and a cannula holder. The clip can comprise stiff arms that are opened by applying pressure to the arms. This enables the patient to attach the device to a fixed object such as clothing or bedding. The cannula holder securely retains the cannula. By retaining the cannula in the cannula holder according to the present invention, less tension and shearing force is transferred from the cannula to a patient's ears, face, neck, or skin. Thus, the subject invention provides a cannula clip that reduces skin discomfort and irritation.

10 Claims, 3 Drawing Sheets

CANNULA CLIP AND ASSOCIATED METHOD OF USE

CROSS-REFERENCE TO RELATED APPLICATIONS

This application claims the benefit of U.S. Provisional Application No. 60/370,795, filed Apr. 8, 2002.

BACKGROUND OF THE INVENTION

Medical patients requiring the administration of oxygen or other gases for extended periods of time generally require the use of a cannula apparatus. A cannula apparatus such as a nasal cannula commonly includes an oxygen-carrying tube having two branches capable of being draped over the ears of a patient. The two tubular branches are joined together in front of the patient's face with a central portion providing two nostril orifices. In order to ensure that the orifices of the nasal cannula remain in registry with the patient's nostrils during use, the two tubular branches of the nasal cannula are typically draped across and supported by the patient's ears. By doing so, the tubular branches function as an earpiece to hold the cannula apparatus in place.

Unfortunately, extensive use of a nasal cannula can irritate and cause great discomfort in the patient. In particular, current nasal cannula apparatuses fail to provide necessary support in relieving the pressure of the cannula from the patient's ears, face, neck, and skin. Thus, discomfort above and behind the patient's ears is a common occurrence. In some cases, discomfort may start off as simple redness and progress to sores or ulcerations above the ears due to the constant rubbing of the tubing against the skin.

Another problem with the use of cannula apparatuses occurs with a freely movable patient. Most mobile patients who require the constant administration of oxygen use at least a 50-foot cannula within their dwellings. Because a longer cannula is required for a freely movable patient, the additional weight from the longer cannula causes a substantial increase in pressure against the skin and areas that support and hold the cannula. Further, because the patient is mobile and the cannula is longer, the cannula will often get caught on furniture or other objects located within the patient's vicinity. A common practice to prevent or alleviate discomfort is to hold the cannula at all times. By holding the cannula, the patient can alleviate the increased pressure generated by the additional length of the cannula as well as to absorb the shock produced when the cannula gets caught on various objects. Since patients must use one hand to hold the cannula as they move about, patients are left with only one free hand to perform activities.

In addition, when a patient is resting or sleeping, it is not unusual for the cannula apparatus to be accidentally displaced or yanked against the patient's ears, face, neck, and skin. This often aggravates any irritation and/or soreness associated with the use of the cannula. Further, if the tubular branches of a nasal cannula are displaced from across the ears, the nostril orifices may move out of registry with the patient's nostrils and render the cannula ineffective for its intended purpose and uncomfortable to the patient.

At the present time, there are a variety of apparatuses available to aid in alleviating these problems. Often, these apparatuses do so by removing the cannula from the patient's ears. Different variations of relief include the use of a skull cap to support and secure the cannula as well a means for securing the cannula to eye glasses. A problem associated with attaching the cannula to eyeglasses or to a skull cap is that the patient cannot comfortably wear the eyeglasses or the skull cap when sleeping. Further, skull caps need to be sized for each user.

Another apparatus currently used to prevent irritation generated by a cannula is a strap-like device adapted to be draped across the top of a patient's head. The strap-like device has two looped end portions through which the tubular branches of the cannula are routed. If the length of the strap-like device is sized appropriately, the tubular branches will be suspended in a spaced relationship above the patient's ears as the strap-like device is draped across the patient's head. By supporting the tubular branches above the patient's ears in this manner, the likelihood that the cannula will irritate or cause discomfort to a patient is reduced.

However, strap-like devices such as the one described above are limited in that when the tubular branches are supported within the end portions of the strap-like device, the tubular portions may shift in position (i.e. in a lengthwise direction) relative to the end portion of the device. Moreover, a strap-like device does little to alleviate the problem of snagging and yanking of the cannula when the patient is mobile.

Also available are ear pads that are placed behind the patient's ears to help alleviate the discomfort of the cannula rubbing against the tender tissue. Because the pads do not provide a means for controlling the tension and pressure created by a cannula, the pads do not entirely alleviate the discomfort associated with the use of a cannula. The pads are sometimes placed over areas already irritated by the cannula, which may slow the healing process around that area. Further, these pads must often be replaced, making them an expensive and inefficient method for addressing the discomfort caused by a cannula.

There are known clips for medical tubing that attach to fixed items such as beds or clothing. The area for holding the medical tubing is not located along the surface of the clip but rather along an elongate strip attached to the clip. By placing the medical tube holder on a strip and not directly on the clip, such devices are less effective in alleviating the pressure generated by the cannula against the patient's skin and ears because the strip can bend under the weight of the cannula or when the cannula is snagged against an object. Further, a restive sleeping patient can dislodge the cannula, or even the elongate strip, thus rendering the clip ineffective for its intended purpose.

Another tube/wire holding device designed for maintaining the position of medical tubes is a mesentery tube holder apparatus with a base plate that would adhere to a patient's skin. A flap with one end permanently affixed to the base plate holds a tube by having an opposite end that adheres to a medical tube. Such fasteners can be difficult to use and ineffective in relieving the pressure of the cannula from the ears. Moreover, the adhesives can irritate skin making such devices undesirable for extended use.

Therefore, there continues to be a need for new and improved apparatuses and methods to secure and support a cannula and alleviate associated discomfort. The present invention overcomes these problems and disadvantages by providing a cannula clip that relieves the discomfort and irritation caused by the weight and rubbing of a cannula against the patient's face, neck, and skin. Further, the cannula clip according to the present invention advantageously secures and alleviates pressure created either from the weight of a longer cannula or from snagging and yanking of the cannula against objects within the vicinity of a freely mobile patient. The method of using the cannula clip is simple and efficient while the cannula clips themselves are easily manufactured.

BRIEF SUMMARY OF THE INVENTION

The present invention provides an apparatus that eliminates the pressure and rubbing of a cannula against a patient's ears, face, neck, and skin. This pressure often causes inflammation, sores, and ulcers around the ears. In a preferred embodiment, the apparatus of the subject invention is a cannula clip comprising any known clip used in attachment to fixed objects such as clothing or bedding and a cannula holder situated on the clip.

When the cannula clip is used, the pressure of the cannula against the ears, face, neck, and skin of a patient is reduced. Advantageously, the cannula clip secures the cannula such that there is no accidental dislodgement of the cannula when the patient is resting or sleeping.

The apparatuses and methods of the subject invention can be used by such institutions as health care facilities and nursing facilities that wish to decrease their spending on such items as ear pads or strap-like devices while improving patient comfort. In addition, ambulatory patients that often use longer cannulae so that they may move about freely without discomfort can use the subject apparatuses and methods. The apparatuses and methods of the subject invention are also advantageous in that they are easy to use by patients or individuals requiring relief from discomfort caused by cannulae.

In one embodiment, specifically exemplified herein, the cannula clip is composed of a spring clip having a pair of elongated members, each with a jaw portion. The elongated members are mounted about a spring assembly that serves as a pivot or fulcrum. The spring assembly unites the elongated members and urges the jaw portions of the clip toward their closed position. A cannula holder is attached to an elongated member. The cannula holder is an open-ended, U-shaped sleeve with a cannula receptacle located at the U-shaped base of the sleeve. The open-ended sleeve has an upper and lower strip, with a bend formed in at least one of the strips to form the cannula receptacle. The cannula holder is attached to the outer surface of an elongated member at either the upper or lower strip of the open-ended sleeve so that the cannula receptacle is located either substantially above or below the clip. In another embodiment, the cannula holder is a C-shaped spring piece with a base end rigidly affixed to an elongated member of the clip.

In a method of use, the cannula holder is inserted over an area of a cannula at least four inches below the site where the tubular branching occurs. Then the clip is attached to a fixed object around the area of the breast bone. In an alternate embodiment, the clip is first attached to a fixed object and then the cannula is inserted into the cannula holder.

An advantageous apparatus is provided by the subject invention that alleviates the pressure of the cannula from the patient's ears, face, neck, and skin. Further, the subject cannula clip provides ease of resting or sleeping because it not only alleviates the pressure of the cannula from the ears, face, neck and skin but it also helps to secure the cannula from accidental dislodgement.

The cannula clip also alleviates any additional pressure associated with a longer cannula when used by a mobile patient. The subject invention also advantageously absorbs the force and pressure generated by a longer cannula when it snags objects within a mobile patient's vicinity. Because the cannula clip alleviates pressure from a longer cannula or from the snagging and yanking of the cannula, a patient now has two free hands to perform activities without worrying about any discomfort or irritation generated by the cannula.

Further, the cannula clip of the subject invention provides a better means for securing and supporting a cannula. By positioning the cannula receptacle either substantially above or below the clip, the cannula clip provides a more effective means for alleviating the pressure exerted by the weight of a cannula or the pressure of a snagged cannula. In addition, there is less likelihood of dislodging the cannula when it is held either underneath or directly on top of the clip versus on an elongate strip.

The present invention also provides a cannula clip that is easy and economical to manufacture. Further the subject cannula clip is uncomplicated in construction and effective in operation. For example, the cannula clip does not need to be adjusted and sized for every user's head.

DETAILED DISCLOSURE OF THE INVENTION

Figure 2:
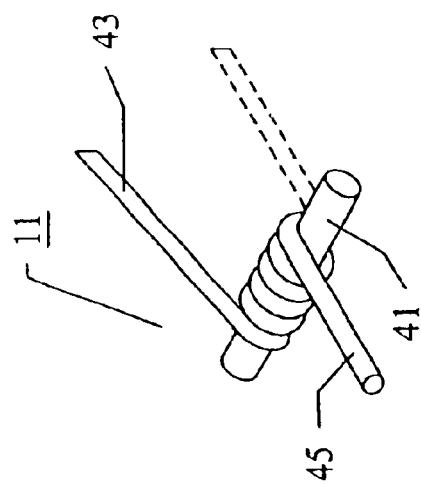
FIG. 2 illustrates a perspective view of the spring loaded pivot pin of the present invention.
Figure 1:
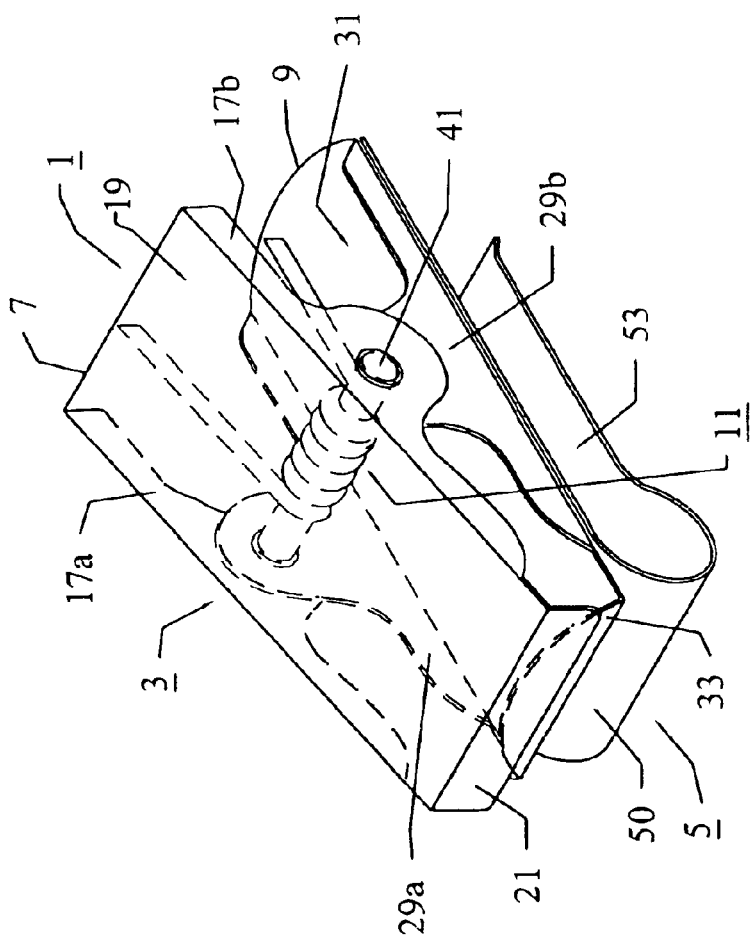
FIG. 1 illustrates a side view of an embodiment of the present invention in a closed position.

FIGS. 1 and 2 illustrate embodiments of a cannula clip according to the subject invention. A cannula clip 1 includes a clip 3 and a cannula holder 5. The cannula clip 1 can be produced from a variety of materials, including metal or plastic. The cannula clip 1 need not be made of a uniform material. Further, the cannula holder 5 may be formed within the cannula clip 1 at manufacture. For example, the cannula clip 1 may be produced from injection molding.

The clip 3 can be a spring clip, such as the one illustrated in FIG. 1, which has a pair of elongated members 7 and 9 and a spring member 11. The elongated member 7 has an outer surface, an inner surface, and a pair of side surfaces 17a, 17b that form a channel 19. At the forward end of the elongated member 7 is a clamping jaw 21 adapted with a bent lip for gripping stationary items. The tail end of the elongated member 7 is adapted for levering the clamping jaw 21 open and closed. The elongated member 9 also has an outer surface, an inner surface, and a pair of side surfaces 29a, 29b that form a channel 31. In addition, the elongated member 9 has a clamping jaw 33 adapted with a bent lip so that articles inserted between clamping jaws 21, 33 may be positively gripped when the lip of clamping jaw 21 closes into clamping engagement with respect to the corresponding lip of clamping jaw 33. Similarly, elongated member 9 includes a tail end adapted to be manually. engaged for levering the clamping jaw 33 open. A spring loaded pivot pin 41 that acts as a pivot or fulcrum interconnects the elongated members 7, 9.

Located on either one of the outer surfaces of elongated members 7, 9 and positioned between the end of clamping jaws 21, 33 and tail ends 23, 35 of the elongated members 7, 9 is a cannula holder 5. The cannula holder 5 is made from a semi-rigid material, such as spring metal or plastic. The cannula holder 5 is a thin, flat sleeve bent back on itself to form a cannula receptacle 50 at the U-shaped base of the sleeve. In an embodiment of the present invention, the passageway 53 created by the sleeve is about ⅜ inch apart. The cannula receptacle 50 is preferably shaped to provide tension to retain a cannula (see for example 55 in FIG. 4).

In an embodiment of the present invention, the cannula receptacle 50 has a diameter that is narrower than the diameter of the cannula 55. The sleeve of the cannula holder 5 is either a non-interrupted form of an elongated member 7, 9 of the clip 3 or is attached to the either one of the outer surfaces of the elongated members 7, 9 using methods known to the skilled artisan. Thus, the cannula receptacle 50 is located substantially above or below the clip 3.

In an embodiment of the present invention, the spring member 11 is a spring loaded pivot pin, as illustrated in FIG. 2, conventionally made from spring metal and includes a helical hollow body portion that surrounds a pin 41 that connects the side surfaces 17a, 17b, 29a, 29b of the elongated members 7, 9 (see FIG. 1). The spring loaded pivot pin 11 also includes a first and second elongated end portions 43, 45. FIG. 2 illustrates the spring member 11 in the relaxed position and the phantom lines show the spring as it is wound to the operative position with the elongated end portion 45 being parallel to and pointing in the same direction as the elongated end portion 43 to provide the conventionally understood spring effect.

As shown in FIG. 1, the elongated members 7, 9 are mounted about the spring member 11 such that the inner surface of the elongated member 7 is disposed opposite and facing the corresponding inner surface of elongated member 9. The channels 19, 31 formed by the side surfaces 17a, 17b, 29a, 29b, houseably receive the spring member 11, in particular the pair of elongated members 43, 45. The spring member 11 is operatively mounted within the clip 3 using pin 41. The elongated members 43, 45, with respect to the elongated members 7, 9, are positioned in the operative position so that the spring member 11 normally urges the clamping jaws 21, 33 toward one another or toward the "closed" position.

In operation, to convert the clip 3 from its nascent position where the clamping jaws 21, 33 are in the closed position, the user must merely apply sufficient pressure to the tail ends 23, 35 of elongated members 7, 9 so that the elongated end portions 43, 45 of the spring member 11 are compressed to urge the clamping jaws 21, 33 away from one another or toward the "open" position. Once in the open position, a fixed object such as clothing or bedding may be inserted into the space created between the clamping jaws 21, 33. Once the desired fixed object is inserted between the open clamping jaws 21, 33, pressure is released from the tail ends 23, 35 so that the natural pressure exerted by the elongated end portions 43, 45 of the spring member 11 urges the clamping jaws 21, 33 into their closed position.

Figure 3:
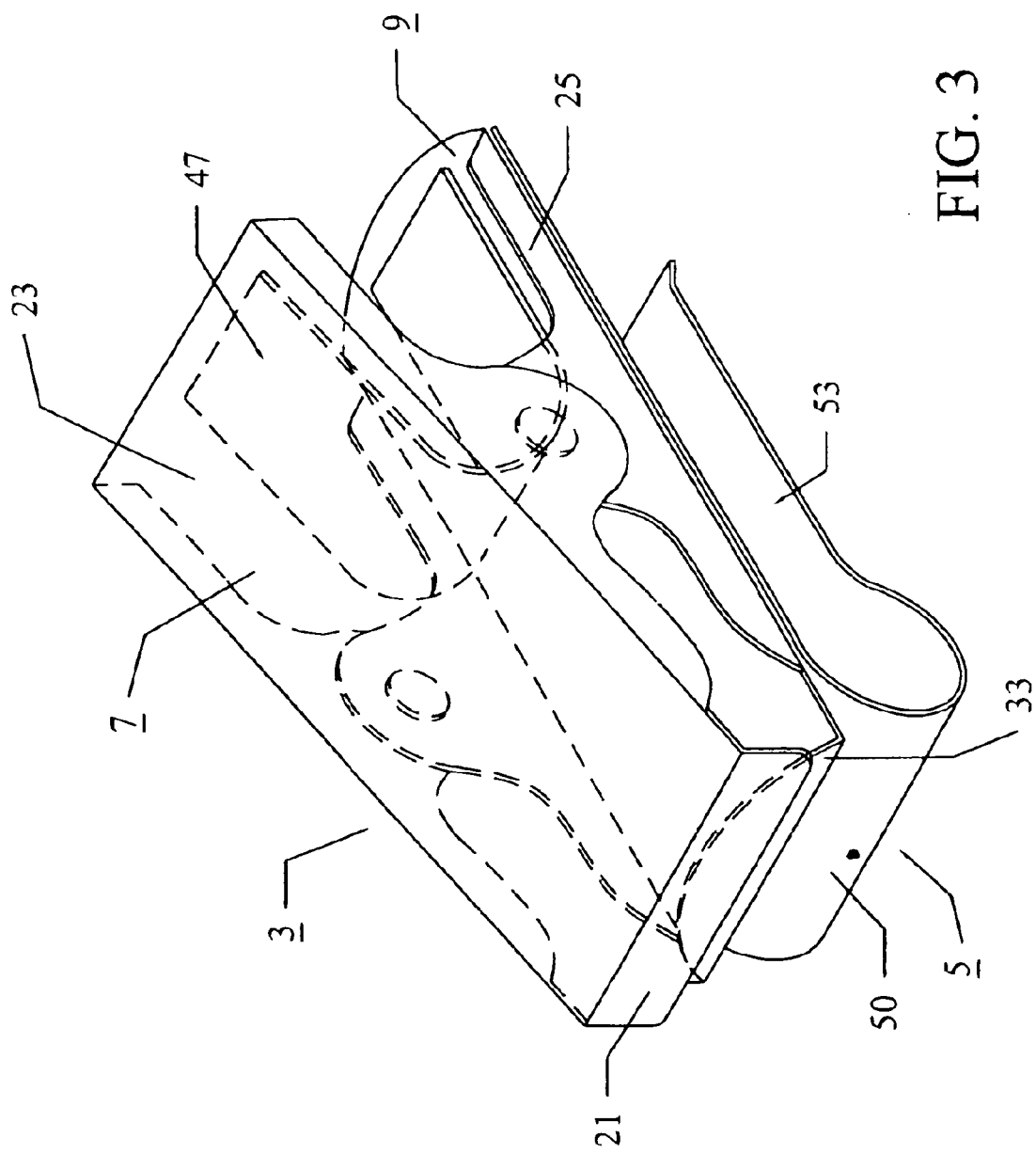
FIG. 3 illustrates a side view of another embodiment of the present invention.

FIG. 3 illustrates a cannula clip, according to the present invention, wherein the clip 3 includes a spring member that is a spring-forming web 47. As with the embodiment illustrated in FIG. 1, the clip 3 includes elongated members 7, 9 which house the spring-forming web 47 that provides a fulcrum for the pivotal movement of the elongated members 7, 9 and that naturally and continuously urges the clamping jaws 21, 33 toward a closed position. The spring-forming web 47 is attached to the clip 3 using methods well-known to those skilled in the art. For example, the spring-forming web 47 may be welded or glued to the inner surfaces of elongated members 7, 9. To open the clip 3 illustrated in FIG. 3, the tails 23, 35 of the elongated members are pressed together to compress the spring forming web 47 to open the compressing jaws 21, 33.

In FIG. 3, located on either one of the outer surfaces of the elongated members 7, 9 is a cannula holder 5. The cannula holder 5 is made from a semi-rigid material, such as spring metal or plastic. The cannula holder 5 is a thin, flat sleeve bent back on itself to form a cannula receptacle 50 at the U-shaped base of the sleeve. In an embodiment of the present invention, the passageway 53 created by the sleeve is about ⅜ inch apart. The cannula receptacle 50 preferably shaped to provide a tension to retain a cannula 55 (see FIG. 4). In an embodiment of the present invention, the cannula receptacle 50 has a diameter that is narrower than the diameter of the cannula 55. The sleeve of the cannula holder 5 either is an integral extension of an elongated member 7, 9 of the clip 3 or is attached to the either outer surfaces of an elongated members 7, 9. Thus, the cannula receptacle 50 is located substantially above or below the clip 3.

Figure 4:
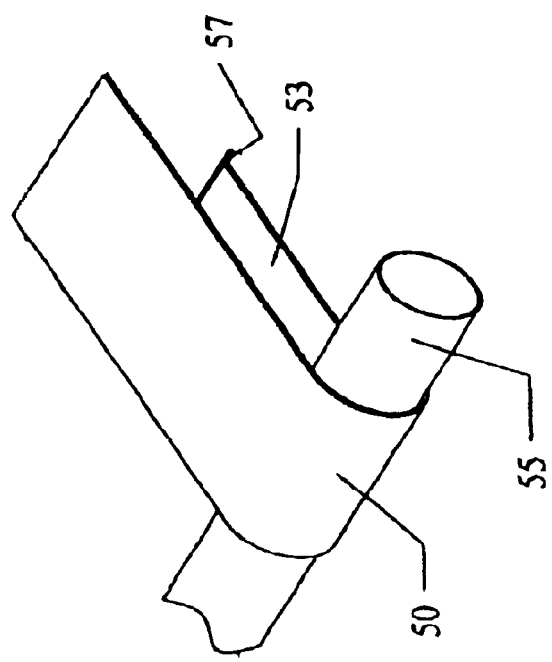
FIG. 4 illustrates an embodiment of a cannula holder for retaining cannula in accordance with the present invention.

Use of an embodiment of the cannula holder 5 is illustrated in FIG. 4. In order to operate a cannula clip, the cannula 55 is inserted into the passageway 53 created by the sleeve and slid into the cannula receptacle 50. The cannula receptacle 50 will secure the cannula 55 from movement while providing support for the tube to alleviate pressure from the weight of the cannula 55. Further, the cannula receptacle 50 secures the cannula 55 without appreciably squeezing or crushing it, thus allowing for proper air flow and prevention of twisting of the cannula 55. An embodiment of the subject invention includes at the end of one side of the sleeve a small bend 57 at roughly 45° that facilitates the introduction of the cannula 55 into the cannula receptacle 50.

Figure 5:
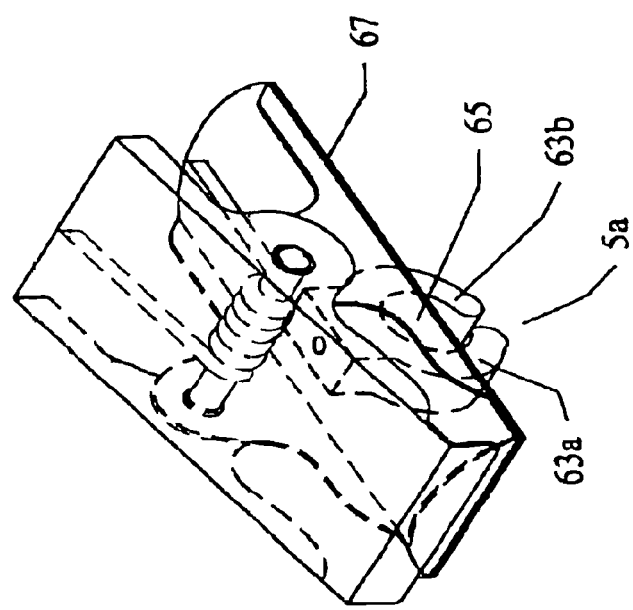
FIG. 5 illustrates an alternative embodiment of a cannula holder.

FIG. 5 illustrates an embodiment of the cannula holder 5. In this embodiment, the spring piece cannula holder 5a includes is an open-ended, C-shaped spring piece having a pair of arms 63a, 63b. The arms 63a, 63b create a cannula receptacle 65 that is preferably sized to provide tension to retain a cannula (not shown). In a related embodiment of the present invention, the cannula receptacle 65 created by the arms 63a, 63b has a diameter that is narrower than the diameter of a cannula. The spring piece cannula holder may be permanently fixed or may swivel (360°) on a base 67 that is rigidly mounted onto a clip 3. The spring piece cannula holder 5a may be attached to a clip (not shown) using methods well-understood by the skilled artisan. For example, the spring piece cannula holder 5a may be glued to the outer surface of the elongated members 7, 9. An additional embodiment provides a cannula clip with the spring piece cannula holder 5a that is an integral extension from either outer surface of elongated members 7, 9. The spring piece cannula holder 5a and the base 67 are made from a semi-rigid material, such as spring metal or plastic. In use, a cannula is inserted into the spring piece cannula holder 5a by pressing the cannula through the entrance created by the arms 63a, 63b to house the cannula in the cannula receptacle 65.

It should be understood that the examples and embodiments described herein are for illustrative purposes only and that various modifications or changes in light thereof will be suggested to persons skilled in the art and are to be included within the spirit and purview of this application.

We claim:

1. An apparatus for alleviating the pressure and rubbing of a cannula against a patient wherein the cannula includes two tubular branches positionable on opposite sides of the patient's head, the apparatus comprising:

a. a clip for releasably attaching the apparatus to a fixed object, wherein the clip comprises a pair of elongated members, wherein each elongated member has an outer surface, a clamping jaw adapted with a bent lip, and a tail end; and b. a cannula holder comprising a cannula receptacle, the cannula holder and the cannula receptacle being located on the outer surface of one of the elongated members and is are entirely positioned between the end of the clamping jaw and the tail end of the one elongate member.

2. The apparatus according to claim 1, wherein
 a. each elongated member further comprises a channel; and
 b. the clip further comprises a spring member, wherein the spring member acts as a pivot and interconnects the elongated members.

3. The apparatus according to claim 2, wherein the spring member is a spring loaded pivot pin including a pin, a helical hollow body portion surrounding the pin, and a pair of elongated end portions, wherein each elongated end portion is situated within the channel of each elongated member so that the natural pressure exerted by the elongated end portions against the elongated members urges the clamping jaws into the closed position.

4. The apparatus according to claim 1, wherein the clip further comprises
 a spring web, wherein the spring web naturally urges the clamping jaws toward a closed position.

5. The apparatus according to claim 1, wherein the cannula holder comprises a thin sleeve bent back on itself, wherein the sleeve includes a U-shaped base, wherein the cannula receptacle is located at the U-shaped base of the sleeve, and a passageway created by the sleeve to operatively receive the cannula.

6. The apparatus according to claim 5, wherein the passageway created by the sleeve measures $3/8$ inch.

7. The apparatus according to claim 5, wherein the sleeve is made from a semi-rigid material.

8. The apparatus according to claim 7, wherein the sleeve is made from plastic.

9. The apparatus according to claim 1, wherein the cannula holder comprises an open-ended C-shaped spring piece and a base, wherein the spring piece comprises a pair of arms to create the cannula receptacle.

10. The apparatus according to claim 9, wherein the spring piece swivels 360° on the base.

* * * * *